United States Patent [19]
Pohle et al.

[11] Patent Number: 5,887,706
[45] Date of Patent: Mar. 30, 1999

[54] FENESTRATED SUTURE PACKAGE

[75] Inventors: Michael S. Pohle, Flemington; Marvin Alpern, Glen Ridge, both of N.J.; Robert J. Cerwin, Pipersville, Pa.

[73] Assignee: Ethicon, Inc., Somerville, N.J.

[21] Appl. No.: 985,497

[22] Filed: Dec. 5, 1997

[51] Int. Cl.⁶ .................................................. A61B 17/06
[52] U.S. Cl. .................. 206/63.3; 206/227; 206/380
[58] Field of Search ................... 206/63.3, 227, 206/380; D9/337, 346

[56] References Cited

U.S. PATENT DOCUMENTS

| | | | |
|---|---|---|---|
| 4,699,271 | 10/1987 | Lincoln et al. | |
| 4,961,498 | 10/1990 | Kalinski et al. | |
| 4,967,902 | 11/1990 | Sobel et al. | 206/63.3 |
| 5,052,551 | 10/1991 | Cerwin et al. | 206/63.3 |
| 5,056,658 | 10/1991 | Sobel et al. | 206/63.3 |
| 5,180,053 | 1/1993 | Cascio et al. | 206/63.3 |
| 5,213,210 | 5/1993 | Cascio et al. | 206/380 |
| 5,230,424 | 7/1993 | Alpern et al. | 206/63.3 |
| 5,236,083 | 8/1993 | Sobel et al. | 206/63.3 |
| 5,249,673 | 10/1993 | Hans-Jurgen F. Sinn . | |
| 5,284,240 | 2/1994 | Alpern et al. | 206/63.3 |
| 5,628,395 | 5/1997 | Daniele et al. | 206/63.3 |
| 5,655,652 | 8/1997 | Sobel et al. | 206/63.3 |

*Primary Examiner*—Bryon P. Gehman
*Attorney, Agent, or Firm*—Selitto & Assoc.

[57] ABSTRACT

A suture package having a shallow polymer tray for holding a suture. The package has a substantially flat floor area, an upturned edge and a plurality of fenestrations therein. The fenestrations cause the package to lay flat by interrupting material stresses set up by, e.g., differential cooling during injection molding. The flatness of the package promotes automated package handling by machines. The fenestrations also save on material usage and disposal while providing the necessary structural integrity for the package.

12 Claims, 2 Drawing Sheets fourth# FENESTRATED SUTURE PACKAGE

FIELD OF THE INVENTION

The present invention relates to packages for storing and dispensing surgical needles and attached suture filaments, and more particularly to a package facilitating automated packaging of armed sutures and which reduces the use and subsequent disposal/recycling of packaging materials.

BACKGROUND OF THE INVENTION

Numerous types of packages and packaging methods have been proposed over the years for economically and reliably delivering or relaying an "armed" suture i.e., a suture having a surgical needle attached, to a surgeon in a sterile condition. Besides maintaining sterility of the armed suture, its packaging must also provide convenient dispensing of the suture under the demanding conditions of surgery. Examples of modern suture packaging are disclosed in U.S. Pat. No. 4,967,902 to Sobel et al. and U.S. Pat. No. 5,052,551 to Cerwin et al. Both of these patents are owned by the assignee herein and disclose a generally oval suture package having a central needle park for holding or "parking" the surgical needle and a peripheral channel for receiving the suture filament attached to the needle. Due to the clearance between successive filament loops and the suture channel, the shape of the channel, and the material composition of the package, the suture can be withdrawn from the package without binding in the suture channel.

Because of the widespread use of armed sutures, their packaging and production occurs on a large scale, such that small changes in their design and/or production methods can generate large implications in terms of the expense and efficiency of production, as well as energy and material costs. For example, production methods and designs that lend themselves to automation not only free human beings from the burden of conducting repetitive, unrewarding, mechanical tasks, but also promote efficient production by utilizing the strength, speed and untiring precision of a machine to perform such tasks. As a result, there is always a desire to utilize methods, materials and designs which are compatible with automation of production. The present invention is directed to that end.

With regard to materials, the common materials used to produce armed suture packaging include thermoplastics, such as, polyethylene and polypropylene, foils, paper and cardboard. Over the years, there has been an increasing demand upon industry for economy in the use of natural resources and restraint in the production and use of materials considered pollutants or merely solid waste that require disposal or recycling. Plastics and other materials derived from petrochemicals have certainly received significant attention with regard to minimization of usage in production as well as minimization of their presence in the finished product. Accordingly, it is an object of the present invention to achieve a reduction in the use of plastics in armed suture packaging.

SUMMARY OF THE INVENTION

The problems and disadvantages associated with the conventional techniques and devices utilized to package and dispense sutures are overcome by the present invention which includes a suture package having a shallow polymer tray for holding a suture. The package has a substantially flat floor area, an upturned edge disposed about the floor area and a plurality of fenestrations therein. The fenestrations cause the package to lay flat and also save on material usage and disposal.

BRIEF DESCRIPTION OF THE FIGURES

For a better understanding of the present invention, reference is made to the following detailed description of an exemplary embodiment considered in conjunction with the accompanying drawings, in which.

DETAILED DESCRIPTION OF THE FIGURES

Figure 1:
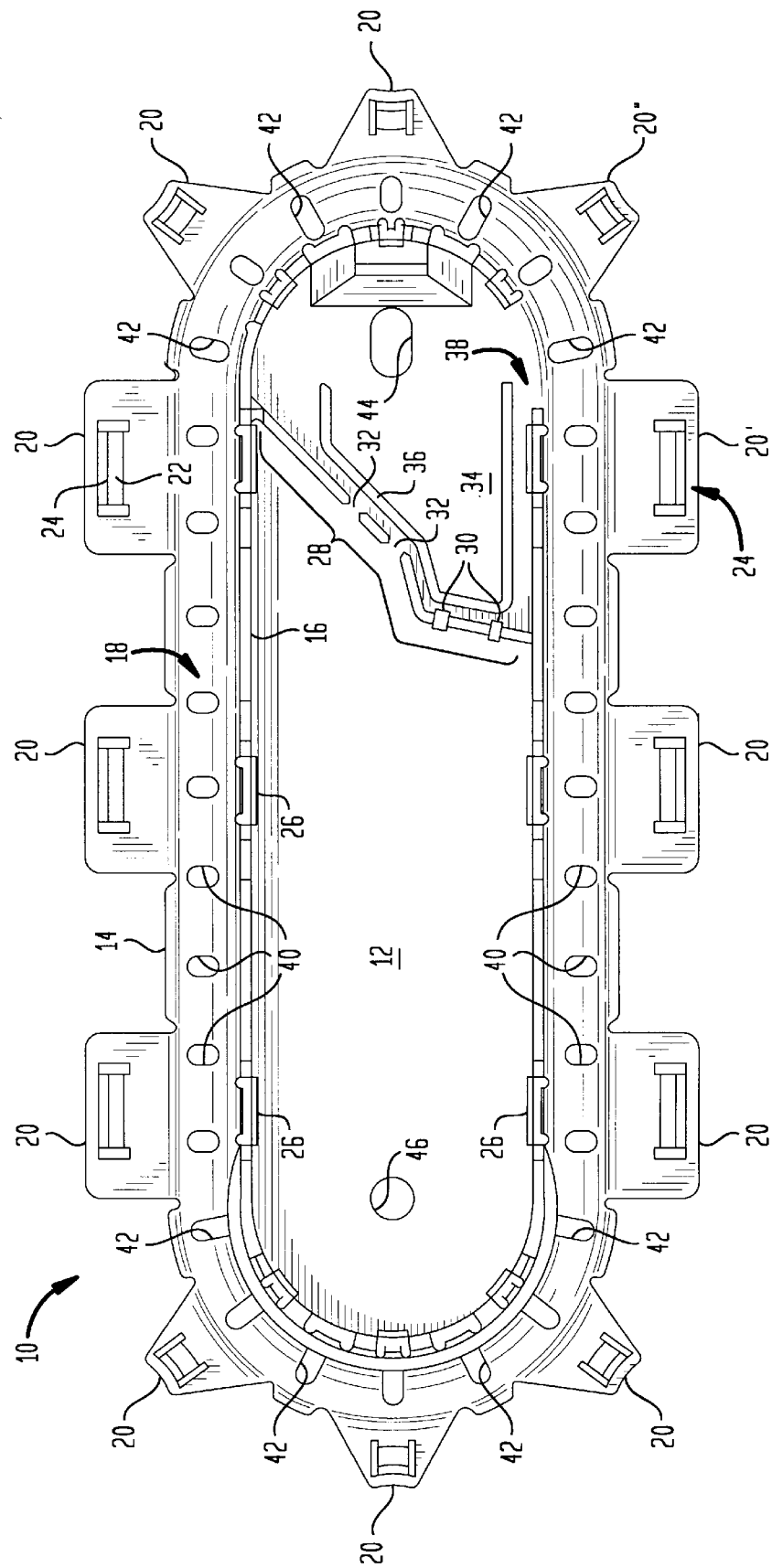
FIG. 1 is a plan view of a prior art suture package.

FIG. 1 shows an empty, unfolded, suture package 10 in accordance with the prior art. The package 10 is primarily a shallow oval pan or tray with a central floor area 12 and a raised edge 14 that curves up from the plane of the floor area 12 to a predetermined height thereabove and to a terminal orientation of about 90 degrees relative to the floor area 12. An inner peripheral wall 16 extends at substantially right angles to the floor area 12 substantially coextensively with the raised edge 14, defining a trough or channel 18 with a generally U-shaped cross-section for receiving a coil of suture filament (not shown). A plurality of suture retaining tabs 20 are hingedly connected, e.g., by "living" plastic hinges, to the raised edge 14 and have latch openings 22 and latch projections 24 to engage mating latch posts 26 projecting from the inner peripheral wall 16. After the suture is laid in the channel 18, the tabs 20 can be bent inwardly and over the channel 18 for retaining the coil of suture filament. The latch projections 24 and latch posts 26 cooperate to retain the tabs 20 in the closed position.

A needle park 28 for holding the surgical needle extends from the floor area 12 proximate one end of the package 10. The needle park includes pairs of undercut and rigid needle holders 30 and 32. The package floor beneath needle holders 30 has been undercut to enable tapered ends of the overlying needle holders 30 to flex and bend somewhat when a needle is inserted therein. Thus, the undercut needle holders 30 can accommodate a wider range of needle gauges than the rigid needle holders 32 can accommodate. Adjacent the needle park 28 is a relief flap 34 defined by a cutout 36. A portion of the inner wall 16 is eliminated in the vicinity of the needle park 28 to form a vent 38 in the channel 18 through which the suture extending from the needle accesses the channel 18 between tabs 20' and 20".

The bottom of the channel 18 is periodically perforated by holes 40 and 42 around the circumference thereof to assist in packaging an armed suture as follows: Package 10 is placed on an assembly platform that has a number of upwardly extending pins. Two of the pins are aligned to extend upward through holes 44 and 46 in the center of the package to retain the package in its assembly position on the platform. Eight other pins extend upward and are aligned to pass through the holes 42 of the channel 18. The platform is open beneath the remaining channel holes 40 and a vacuum source below the platform draws air through the holes 40. With the package so emplaced, the needle is located in one of the needle parks 30, 32, of the needle holder 28, and the suture is looped above the pin extending through hole 44 then downward through the vent 38 and into the suture channel 18. The suture is then wound in a clockwise direction around the pins which extend through the channel holes 42.

Additional details regarding the construction and use of the suture package of FIG. 1 appear in U.S. Pat. Nos. 4,967,902 and 5,052,551. Both of these patents are incorporated herein by reference.

The sutures which may be packaged in the packages shown in FIG. 1 include any of the conventional sutures, absorbable and non-absorbable, such as silk, polypropylene, polydioxanone, and the like and equivalents thereof. The sutures may be braided, woven or monofilament and the needles may be tapered or cutting point, curved, semi-curved, or straight. The sutures are typically mounted to the ends of surgical needles by conventional processes such as swaging.

A variety of materials can be used to form the suture package described in relation to FIG. 1 above, including polyester, polyethylene, polyvinyl chloride, polystyrene and polypropylene and, in general, it is desirable to utilize different materials for the packaging than for the sutures to prevent "gauling" or "lock-ups" when the suture is removed from the package.

As can be appreciated from FIG. 1, the suture package 10 is asymmetrical in the direction of extension of the inner peripheral wall, i.e., in the viewing direction of the plan view, due to the fact that all the features of the package extend unidirectionally from the floor area 12 of the package. More specifically, the inner wall 16, the needle park 28, the peripheral edge 14, etc. all extend in the same direction away from the floor area 12. As a result of the foregoing asymmetry, packages manufactured using conventional thermoplastic forming methods, such as injection molding, tend to have inherent unbalanced internal stresses, such as those produced by uneven cooling, leading to warpage and distortion of the package from its intended design configuration.

While the warpage in packages made in accordance with the prior art can be overcome by additional packaging layers, such as overwraps etc., such that it does not effect the operation or acceptability of the final product, it does lead to production difficulties, in that the warpage is unpredictable and tends to cause malfunctions and misalignments when warped packages are processed by automated machinery. While it would be desirable to use the same molding equipment to produce packages of the same configuration but different composition, it has been observed that different materials cause different warping conditions. For example, polyethylene exhibits greater shrinkage on cooling than polypropylene leading to variations between the warpage of packages made from these two materials. As a result, even if the automated processing equipment were designed to process warped packages, different materials would each require specialized automated handling equipment and/or associated special settings and adjustments. Clearly, automata work best when the work pieces are uniform.

Figure 2:
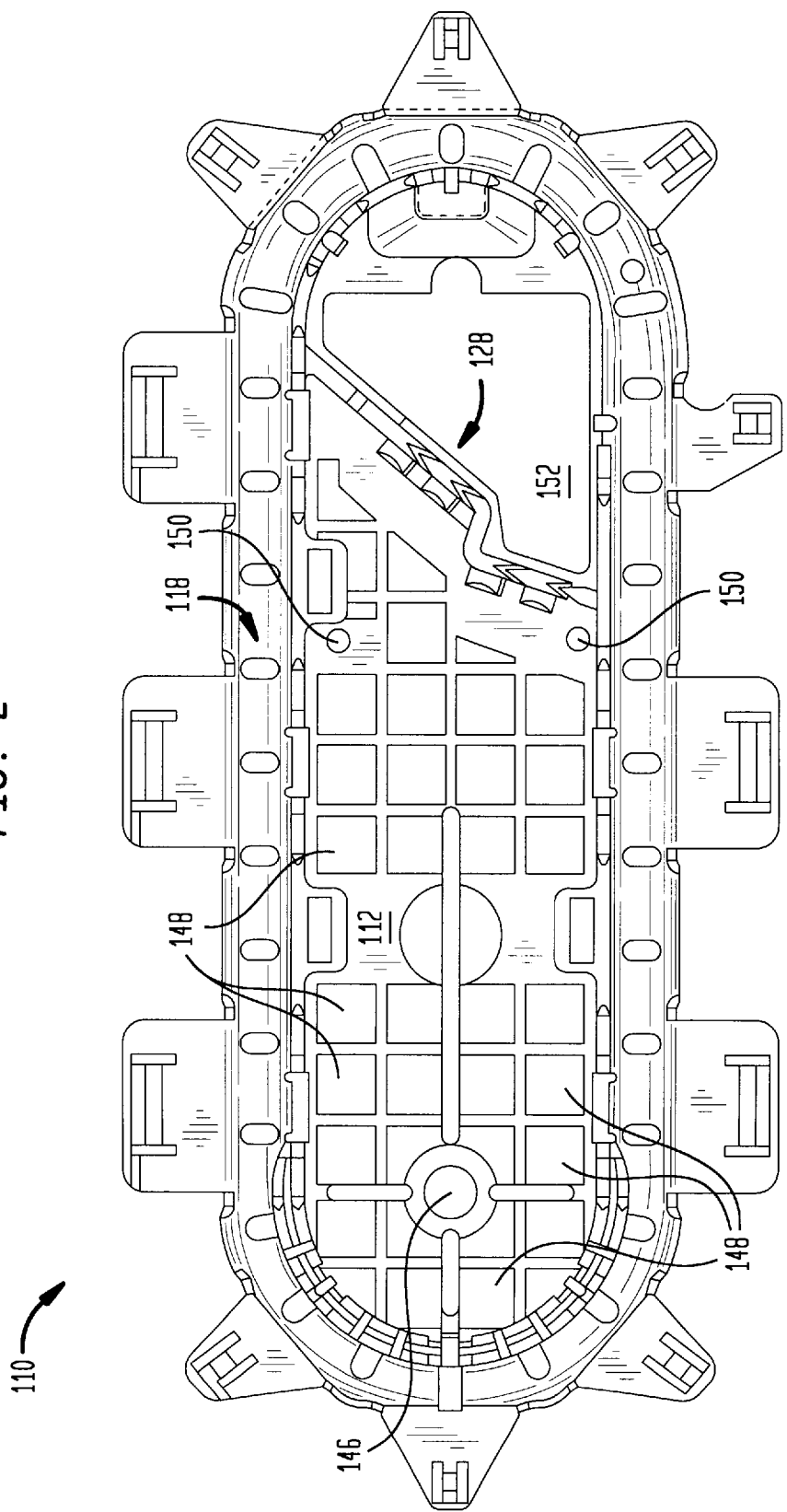
FIG. 2 is a plan view of a suture package in accordance with the present invention.

FIG. 2 shows a suture package 110 in accordance with the present invention. One can readily appreciate from comparing FIG. 2 to FIG. 1 that there are substantial similarities between the prior art device and the present invention. To more clearly illustrate the relationship between FIGS. 1 and 2, a numbering convention is adapted herein in which elements of the invention depicted in FIG. 2 which are similar to those depicted in FIG. 1 are given the same reference number increased by 100.

With the foregoing prefatory comments in mind, the primary difference between the present invention and the prior art depicted in FIG. 1 is the presence of a plurality of fenestrations 148 in the central floor area 112. The fenestrations 148 are structural openings extending through the central floor area 112 and may be square, triangular, pentagonal, hexagonal or any other shape which results in a workable open area ratio while preserving structural integrity of the package, i.e., there should not be excessive flexure of the package while in normal use for dispensing armed sutures. It is preferred that the fenestrations 148 be formed in the package 110 as part of the original molding process rather than being perforated or die cut into a non-fenestrated package. This method of formation of the fenestrations is consistent with one of the objectives and benefits of the present invention, namely, that the fenestrations 148 result in a decrease in material usage for forming the package 110 and a corresponding decrease in the amount of waste product represented by the package itself. For example, the package 110 of FIG. 1 uses at least 15% less polymer than an otherwise identical, non-fenestrated package. The economy of material usage associated with the present invention results in a lighter product which costs less to ship and handle relative to its non-fenestrated counterpart.

Besides the foregoing beneficial attributes, the present invention is also typified by a suture package 110 that lies flat and which does not exhibit the warpage associated with prior art packages. The flat configuration of the present invention is maintained regardless of the materials that are used to form it and is thought to be due to the fenestrations interrupting the transfer of internal material stresses, such that the package assumes and retains its designed shape without warpage. For example, one can observe that the fenestrated package 110 of FIG. 1 in practice diverges by no more than 10% from the design configuration in height, length and width. As can be appreciated from FIG. 2, the fenestration of the suture package 110 must be carried out selectively so as not to weaken the package in its support of the various features that permit its production and use. For example, the fenestrated central floor area 112 of the present invention constitutes a suitable structural network for supporting the needle park 128 and alignment hole 146 which is used for positioning the package in a suture winding machine for laying the suture in the channel 118. Similarly, areas of the central floor 112 which interact with the injection molding machinery must be preserved, for example, areas 150 constitute push-off spots for ejecting the molded part from an injection molding machine. In order to achieve a substantial attenuation of internal stresses, it is necessary that the floor area 112 have an open area to closed area ratio of at least 20% to 80%.

Floor area 112 has an enlarged aperture 152 proximate needle park 128 to facilitate removal of a surgical needle from the needle park by either left-handed or right-handed surgeons. More specifically, removing the needle from the front yields a first needle orientation suitable for a right-handed surgeon and removal from the back yields a second needle orientation suitable for a left-handed surgeon. More details of this universal needle dispensing and orientation feature of the needle package 110 depicted herein are set forth in a co-pending application by the inventors hereof and entitled, ARMED SUTURE PACKAGE WITH UNIVERSAL DISPENSING CAPABILITY Ser. No. (not yet assigned) which was filed contemporaneously herewith and is incorporated by reference herein.

Some of the benefits of the fenestrations 148 of the present invention are realized when processing the suture packaging 110 in automated machinery, such as, during the application of paper lids to the suture package 110 after the tabs 120 have been locked in place to retain the suture material in the channel 118, as described in, e.g., U.S. Pat. No. 4,967,902. More particularly, the fenestrated package 110 according to the present application lies flat and therefore feeds cleanly into the lid applying apparatus without jamming the machine or otherwise interrupting production.

The paper lid on the open upper side of the suture package 110 is imprinted with an identification of the suture material contained in the package, as well as other identification information such as lot number and manufacturer identification.

The suture package 110 is completed for shipping by overwrapping with foil and alternatively with a polymer film. Overwrapping of this type is well known in the field, as are the proper procedures for maintaining sterility of the suture during the assembly of the sealed suture package. Accordingly, such conventional processes shall not be described herein. When the suture package is used, the plastic overwrapping, if provided, can be removed in the non-sterile field. The foil wrapping can then be removed in the course of transfer from the non-sterile field to the sterile field, for example, the circulating nurse can strip back the foil wrapping and the scrub nurse can withdrawal the suture package from the foil overwrapping and place it on a mayo stand. As a consequence, neither the surgeon nor the scrub nurse is required to tear open the suture package in the sterile field. The suture package can therefore be described as offering a one-step presentation. Because the package is overwrapped in foil, sterility is preserved notwithstanding the fenestrations 148 in the central floor area 112.

It should be understood that the embodiments described herein are merely exemplary and that a person skilled in the art may make many variations and modifications without departing from the spirit and scope of the invention as defined in the appended claims. For example, whereas the present disclosure describes the invention herein as including fenestrations in the central floor area 112, the present invention could also encompass fenestrations in other parts of the suture package, for example, additional fenestrations could appear in the suture channel area 118 or in the locking tabs 120. The fenestrations can be of any shape or dimensions so long as they preserve the structural integrity of the package while providing the intended benefits of the invention. Whereas a generally oval-shaped suture package is shown in the application, other package shapes, such as circular or polygonal, could be employed. All such variations and modifications are intended to be included within the scope of the invention as defined in the appended claims.

We claim:

1. A suture package, comprising a shallow polymer tray for holding a suture and having a substantially flat floor area, an upturned edge disposed about said floor area, a peripheral inner wall projecting at about 90 degrees from said floor area and positioned between said floor area and said upturned edge, said inner wall and said upturned edge defining a suture channel, and a needle park disposed on said floor area, said floor area bounded by said inner wall and said needle park and having a plurality of fenestrations therein a lattice pattern and occupying at least 50% of said floor area.

2. The package of claim 1, wherein said fenestrations are multiple, square in shape and are arranged in regular rows and columns.

3. The package of claim 1, wherein said package is a product of an injection molding process and wherein said floor area is substantially flat when it emerges from a mold utilized to form said package.

4. The package of claim 3, wherein said floor area is fenestrated and has pushpoints for disengaging said package from a mold after its formation by injection molding.

5. The package of claim 1, wherein said needle park is positioned upon a structural member extending between opposing portions of said peripheral inner wall.

6. The package of claim 1, wherein said package is generally oval.

7. The package of claim 1, wherein said fenestrations are dimensioned and positioned to interfere with the transfer of internal stresses that would otherwise distort said floor area from a flat configuration.

8. The package of claim 1, wherein said package is formed from polyethylene and said floor area is substantially flat when it emerges from a mold utilized to form said package.

9. The package of claim 1, wherein said package is formed from polypropylene and said floor area is substantially flat when it emerges from a mold utilized to form said package.

10. The package of claim 1, wherein said package uses at least 15% less polymer material than an otherwise identical, non-fenestrated package.

11. The package of claim 1, wherein said package is sufficiently dimensionally stable to be automatically labelled by a mechanized assembly line subsequent to its formation and without manual manipulation of said package.

12. The suture package of claim 1, wherein said fenestrations are dimensioned and positioned to interrupt the transfer of internal stresses that would otherwise distort said floor area from a flat configuration, said suture package further comprising a plurality of suture retaining tabs hingedly connected to said upturned edge and bending inwardly toward said peripheral inner wall; a paper label disposed over said suture package for identifying a suture contained therein; and a foil overwrap for maintaining the sterility of a suture contained therein and accessible to a surgeon upon the removal of said foil overwrap to provide a one step presentation.

* * * * *